United States Patent [19]

Hazen et al.

[11] Patent Number: 5,102,442
[45] Date of Patent: Apr. 7, 1992

[54] ANTAGONISM DEFEATING CROP OIL CONCENTRATES

[75] Inventors: James L. Hazen, Apex; Rudolf H. A. Frank; Paul S. Zorner, both of Durham, all of N.C.; James R. Campbell, Bud Lake, N.J.

[73] Assignee: BASF Corporation, Parsippany, N.J.

[21] Appl. No.: 624,489

[22] Filed: Dec. 6, 1990

Related U.S. Application Data

[60] Continuation of Ser. No. 323,771, Mar. 15, 1989, abandoned, which is a division of Ser. No. 107,658, Oct. 5, 1987, Pat. No. 4,834,908.

[51] Int. Cl.$^5$ .................. A01N 43/88; B01F 17/30
[52] U.S. Cl. .......................................... 71/91; 71/123; 71/DIG. 1; 252/356
[58] Field of Search .................. 71/DIG. 1, 91, 123; 252/356

[56] References Cited

U.S. PATENT DOCUMENTS 4,249,937  2/1981  Iwataki et al. ..................... 71/97
4,447,257  5/1984  Gerwick, III ..................... 71/91
4,666,510  5/1987  Watson et al. ..................... 71/103

FOREIGN PATENT DOCUMENTS 79774  5/1983  European Pat. Off. .
6810762  2/1970  Netherlands ............... 71/DIG. 1

OTHER PUBLICATIONS

Thomson, *Agricultural Chemical, Book II Herbicides* (1983–84 Revision) (1983, Thomson Publications), pp. 238–239.
McCowan, "Turf Herbicide Rx: Add Oil," *Agricult. Chem.* (23)4, Apr. 1968.
Chemical Abstracts of (for record) CA (99) 117863u.
Rhodes, et al. "Influence of Bentazon on Absorption and Translocation of Sethoxydim in Goosegrass" *Weed Science* 32:595–97 (1984).

Primary Examiner—Richard L. Raymond
Assistant Examiner—B. M. Burn

[57] ABSTRACT

Crop oil concentrates are disclosed which not only increase the herbicidal efficacy of herbicides from diverse chemical classes, but moreover assist in defeating the apparent antagonism which often arises when two or more herbicides are utilized together.

4 Claims, No Drawings

ANTAGONISM DEFEATING CROP OIL CONCENTRATES

This is a continuation of copending application Ser. No. 07/323,771 filed on Mar. 15, 1989, now abandoned, which is in turn a divisional of Ser. No. 07/107,658, filed Oct. 5, 1987, now issued U.S. Pat. No. 4,834,908.

BACKGROUND OF THE INVENTION

1. Field of the Invention

The subject invention relates to crop oil concentrates. More particularly, the subject invention relates to improved crop oil concentrates which enhance the efficacy of herbicides, and which defeat the antagonism which often results when two or more herbicides are used in combination.

2. Description of the Related Art

It is well established that a variety of adjuvants play important roles in the application of herbicides. These adjuvants are a diverse group of components with equally diverse functions which may often be determined from their generic names, i.e. "spreaders," "stickers," "solubilizers," "emulsifiers," "flow control agents," "drift control agents," and so on. Among the many useful herbicide adjuvants are the so-called "crop oil concentrates."

Crop oil concentrates are often recommended by herbicide manufacturers and formulators for inclusion in tank mixes to increase the efficacy of postemergent herbicide formulations. Crop oil concentrates are available from a variety of sources, and generally consist of from 75-95 percent by weight of a hydrocarbon oil or solvent with the balance being a surfactant. The hydrocarbons which form the bulk of the crop oil concentrate may be derived from mineral (petroleum) or vegetable sources. For example, U.S. Pat. No. 3,990,884 discloses an herbicide system containing, in addition to the 4-chloro-2-butynyl-m-chlorocarbanilate active ingredient, from 10-30% by weight of an oxyethylated fatty alcohol, 5-15% of calcium dodecylbenzene sulfonate and 25 to 75% of a hydrocarbon oil.

Although the use of selected crop oil concentrates may enhance herbicidal efficacy, it is well known that many of the proprietary concentrates available are not as effective as others. Some may even impact negatively upon herbicidal efficacy. Additionally, there is a great deal of inconsistency with regard to the make up of available crop oil concentrates. Finally, to further complicate the situation, manufacturers frequently change the formulations without notifying the consumer, resulting in a great deal of uncertainty with regard to their performance.

In recent years, the situation with respect to crop oil concentrates has achieved such a level of notoriety that some agriculturists refer to them as "snake oils." Thus there is a need in the agricultural sector, for a crop oil concentrate with a well defined make-up which is capable of enhancing the efficacy of a broad spectrum of herbicides, and which gives reproducible results.

SUMMARY OF THE INVENTION

It has now been surprisingly discovered that certain crop oil concentrates enhance activity of a broad spectrum of herbicides to an unexpectedly high level, and moreover these same crop oil concentrates surprisingly defeat the antagonism which is often created when two or more herbicides are utilized simultaneously.

DESCRIPTION OF THE PREFERRED EMBODIMENTS

The crop oil concentrates of the subject invention comprise a mixture of (a) a lower alkanol ester of a long chain carboxylic acid; (b) an anionic surfactant derived from esterification of a polyoxyalkylene nonionic surfactant with a dihydric or trihydric inorganic acid or by carboxylation with an organic acid derivative; (c) a long chain carboxylic acid; and (d) a hydrocarbon component.

The lower alkanol ester of the long chain carboxylic acid (a) may be considered as derived from a lower alkanol having from 1 to 4 carbon atoms, such as methyl alcohol, ethyl alcohol, propyl alcohol, or butyl alcohol, and a long chain carboxylic acid. The methyl and ethyl esters are preferred. Most particularly, the methyl esters are utilized. The long chain carboxylic acid generally contains from 10–20 carbon atoms, preferably from 14–18 carbon atoms. Preferred are those carboxylic acids obtainable from natural sources such as fats and oils, for example lauric, myristic, stearic, linoleic, linolenic, palmitic, and oleic acids. Mixtures of these acids are also useful. Preferred are oleic and palmitic acids and their mixtures. Thus the most preferred alkanol esters are methyl oleate, methyl palmitate, and mixtures of these esters. In the remainder of the specification, such compounds will be referred to as lower alkanol esters.

The anionic surfactants (b) which are useful in the practice of the subject invention are preferably the partial sulfate and phosphate esters of polyoxyalkylene ethers. These partial esters are prepared by methods well known to those skilled in the art, for example by reacting one of the well known and commercially available monohydric polyoxyalkylene ethers with sulfuric acid or phosphoric acid or their chemical equivalents. The sulfate esters so obtained consist predominately of the half ester (monoester) while the phosphate esters generally contain both mono- and diesters. Also useful, are the carboxylate surfactants.

The methods of preparation of such surfactants are well known to those skilled in the art. The sulfate esters may be prepared, for example, by reacting a suitable monofunctional polyoxyalkylene ether with sulfuric acid or its chemical equivalent, preferably sulfamic acid or sulfur trioxide. The phosphate esters may be prepared similarly by reaction of the monofunctional polyoxyalkylene ether with phosphoric acid, diphosphorus pentoxide, polyphosphoric acid, or phosphorus oxytrichloride. Methods of preparation are described in the treatise *Nonionic Surfactants*, Martin Schick, Ed., Marcel Dekker, New York, ©1967, in Chapter 11, pp 372-394.

The nonionic, monofunctional polyoxyalkylene ethers used to prepare the sulfate and phosphate esters are also well known to those skilled in the art, and are available commercially from many sources. Preferred nonionic, monofunctional polyoxyalkylene ethers have molecular weights of from about 400 to about 3000 Daltons, more preferably from about 600 to about 1200 Daltons, and particularly about 800 Daltons.

The preferred polyethers are prepared by oxyalkylating a monofunctional initiator by known methods. Preferred initiators are the alkylphenols such as octyl- and nonylphenol, and the aliphatic alcohols, particularly the latter. The preferred aliphatic alcohols have from 6 to 30, more preferably from 10 to 20, and in particular, from 12 to 16 carbon atoms in the aliphatic residue.

The alkylene oxides which may be used to prepare the nonionic monofunctional polyoxyalkylene intermediates include ethylene oxide, propylene oxide, and butylene oxide. Tetrahydrofuran may also be useful. Preferred alkylene oxides are ethylene oxide and propylene oxide. When both these oxides are utilized, they may be added simultaneously, in sequence, or in combinations of these modes of addition, to prepare block, heteric, and block-heteric surfactants. Ethylene oxide may also be used alone to form homopolymeric polyoxyethylene polyethers.

The carboxylate surfactants are derived from oxyethylated alipatic alcohols by reaction with chloroacetic acid in the presence of base. The preparation is described in the Schick treatise, supra, at pages 388–89. Preferably, the aliphatic alcohol contains from 8 to 18, more preferably from 10 to 14 carbon atoms, and is oxyethylated with from 2 to 10, preferably from 3 to 8 moles of ethylene oxide. Preferred is the carboxylate formed from the reaction of chloroacetic acid and the four mole oxyethylate of lauryl alcohol. Reference in the specification and the claims to "carboxylates" of monohydroxyl functional polyoxyalkylene ethers is to this type of surfactant.

The long chain carboxylic acid (c) may have a chain length, of from 10 to 20 carbon atoms. Preferably, the carboxylic acid is selected from the group of naturally occurring fatty acids such as stearic acid, linoleic acid, linolenic acid, palmitic acid, oleic acid, and the like and mixtures thereof. The unsaturated fatty acids are preferred. Most preferably, the organic acid is oleic acid. The long chain carboxylic acid may be added as an individual component, or it may be derived from the in situ hydrolysis of the lower alkanol ester (a). It is preferable to add the long chain carboxylic acid as an individual component and thus substantially avoid changes in the overall composition over time due to ester hydrolysis.

Components (a), (b), and (c) may be used alone as the crop oil concentrate. However, in such a case, the viscosity of the concentrate is higher than is desirable. Furthermore, at low temperatures, certain of the components of the concentrate may precipitate to some degree. Such low temperatures are often encountered in the northernly climates or in the early spring Hence it is desirable that component (d), the hydrocarbon component, be added to decrease the viscosity of the concentrate and to help prevent component separation at low temperatures.

The hydrocarbon component (d) may be derived principally from vegetable or petroleum sources. Preferred are the aromatic solvents particularly those containing alkylated benzenes and naphthalenes. Such solvents are readily available from a number of sources, for example, the Shellsolve ® solvents available from the Shell Oil Co., Houston, Tex., and the Aromatic ® 150 and 200 solvents available from the Exxon Corporation. The hydrocarbon component may also contain up to about 30 percent by weight, preferrably from 10–30 percent by weight of a solvent soluble alcohol, for example isooctanol, to maintain or enchance the physical properties of the blend. Other solvent soluble alcohols which are suitable are those which generally contain from 5 to about 18 carbon atoms, preferably from 5 to about 10 carbon atoms. The term "hydrocarbon component" as used herein should be taken as including both aliphatic and aromatic solvents as well as their mixtures, including also the solvent soluble alcohol component described immediately above. The hydrocarbon component is believed to exert some biochemical effect in concert with that of the remaining ingredients, and hence may be considered an active ingredient.

When utilized as a crop oil concentrate without the hydrocarbon component, the composition generally contains, in percent by weight relative to the total weight of the concentrate, from 20 to 90 percent lower alkanol ester, 4 to 40 percent anionic surfactant, and 2 to 20 percent fatty acid. Preferably, the composition contains 30 to 80 percent lower alkanol ester, 4 to 20 percent surfactant, and 4 to 16 percent fatty acid. Most preferably it contains 70 to 80 percent lower alkanol ester, 10 to 20 percent surfactant, and 8 to 14 percent fatty acid.

The prefered hydrocarbon component-containing crop oil concentrates generally contain, in percent by weight relative to the total weight of the crop oil concentrate, from about 10 to about 60 percent of lower alkanol ester, from about 2 to about 20 percent anionic surfactant, from 1 to about 10 percent fatty acid, and from 70 to about 30 percent hydrocarbon component. More preferably, the crop oil concentrate contains from 25 to 45 percent lower alkanol ester, 2 to about 10 percent anionic surfactant, 2 to 8 percent fatty acid, and 60 to 40 percent hydrocarbon component. Most preferably, the crop oil concentrate contains from about 35 to about 40 percent lower alkanol ester, from about 5 to about 10 percent anionic surfactant, from about 4 to 7 percent fatty acid, and about 50 percent hydrocarbon component. The hydrocarbon component may optionally contain up to about 30 percent, preferably from 10 to about 20 percent, and most preferably about 18 percent of a solvent soluble alcohol.

The crop oil concentrates of the subject invention may be utilized in many postemergent herbicide formulations, generally in amounts of from about 0.5 to about 8 l/ha, preferably from about 2 to about 5 l/ha. Many manufacturers recommend the use of crop oil concentrates for particular applications or, in some cases, for all applications of their herbicides. In other cases, the concentrates may be used as experience dictates. The crop oil concentrates of the subject invention have been found effective with herbicides of diverse chemical structure, for example with the cyclohexenone herbicides, with benzothiadiazinonedioxide herbicides, with diphenylether herbicides, with dipyridilium herbicides and with aryloxyphenoxy herbicides including analogues containing heterocycles such as the quinoxalinyloxyphenoxy herbicides. The crop oil concentrates are especially effective with the cyclohexenone-type herbicides, and particularly when these herbicides are used in conjunction with herbicides of other classes.

The cyclohexenone herbicides with which the subject invention crop oil concentrates may be used are well known. Examples of their preparation and use may be found in U.S. Pat. Nos. 3,950,420; 4,011,256, 4,249,937, and 4,666,510. Specific mention may be made of certain of the more common cyclohexenones, including alloxydim, sethoxydim, cycloxydim, clethodim, and cloproxydim.

The diphenyl ether herbicides and their analogues are likewise well known. These herbicides are described, for example, in chapter 14 of *Herbicides,* P.C. Kearney et. al., published by Marcel Dekker, Inc., New York © 1976. Many other classes of herbicides are also described in this two volume treatise. Also well known are the dipyridilium herbicides such as paraquat, diquat, and morfamquat.

In the examples which follow, herbicides or herbicide mixtures are tested for their efficacy against a variety of common weeds. In many cases, comparisons are made to similar compositions containing other crop oil concentrates. The "standard" crop oil concentrate used for comparison purposes is "Booster Plus E," a product of the Agway Corporation. This product has been widely used in herbicide applications and appears to have consistent formulation and product quality. In the examples, this "standard" crop oil concentrate is labeled "OC". In certain cases, sunflower oil methyl ester, nonionic surfactants, or other crop oils are compared to the subject invention crop oil concentrates. In all the tables showing efficacy of the crop oil concentrate/herbicide mixtures against various species of weeds, the numerical values in the tables represent the percentage of weed control, or percent kill of the various species. The term "Concentrate" is used to represent "crop oil concentrate" in these tables.

EXAMPLES 1-3

Crop oil concentrates COC-1, COC-2, and COC-3 were prepared by mixing together the following ingredients in parts by weight:

|  | COC-1 | COC-2 | COC-3 |
|---|---|---|---|
| C-65 ® methylester[1] | 37.5 | 37.5 | 30.0 |
| Klearfac ® AA270 anionic surfactant[2] | 7.5 | 7.5 | 15.0 |
| Oleic acid | 5.0 | 5.0 | 5.0 |
| Aromatic ® 150 solvent[3] | 50.0 | 42.5 | 35.0 |
| Isooctanol | — | 7.5 | 15.0 |
|  | 100.0 | 100.0 | 100.0 |

[1]C-65 ® methylester is a product available from the Stepan Chemical Co. It is an approximately 1:1 blend of methyloleate and methylpalmitate derived from natural sources.
[2]Klearfac ® AA270 is a phosphate ester surfactant derived from a nonionic polyether having a molecular weight of about 800 Dalton. It is available from BASF Corp., Parsippany, N.J.
[3]Aromatic ® 150 solvent is a mixed aromatic solvent available from the Exxon Chemical Corporation.

In comparing the efficacy of the subject invention crop oil concentrates with alternative crop oil concentrates, the respective concentrates were added at levels of generally from 2 to 5 l/ha to tank mixes of the herbicides and agitated to prepare a uniform mixture. Cyclohexenone herbicides A, B, C, and D are experimental cyclohexenones of the type disclosed in U.S. Pat. Nos. 4,249,937, 4,011,256, and 3,950,420.

Standard abbreviations for the various weed species found in the text which follows may be found below:
AVEFA *Avena fatua* wild oats
AVESA *Avena sativa* oats (volunteer)
BRAPP *Brachiaria platyphylla* broadleaf signal grass
BROSE *Bromus secalinus* ryebrome
CHEAL *Chenopodium album* fat hen
DAOTE *Daubentonia texana* coffee weed
DATST *Datura stramonium* thorn-apple
DIGSA *Digitoria sanguinalis* large crabgrass
ECHCG *Echinochloa crus-galli* barnyard grass
FESAR *Festuca arundinacea* tall fescue
HORVU *Hordeum vulgare* barley (volunteer)
IPOLA *Ipomoea lacunosa* pitted morning glory
LEFFI *Leptochloa filiformis* red sprangletop
LOLMU *Lolium multiflorum* annual ryegrass
PANTE *Panicum texanum* witchgrass
POAAN *Poa annua* meadow grass
POAPR *Poa pratensus* smooth meadow grass
SETFA *Setaria faberii* giant fox tail
SETLU *Setaria lutescens* yellow foxtail
SETVI *Setaria viridis* green foxtail
SORHA *Sorghum halepense* Johnson grass
TRZAX *Triticum aestivum* wheat (volunteer)
XANPE *Xanthium pennsylvanicum* cocklebur
ZEAMX *Zea mays* corn (volunteer)

Herbicide mixtures are frequently used in weed control. Often, one selective herbicide will show great efficacy in controlling several weed species but will have little effect on others. When complete weed control is desired either sequential application of two or more herbicides is required or one application of a mixture of two or more herbicides is required. Successive herbicide application is not cost-effective. However, the use of mixtures of herbicides often fails to achieve the desired results due to apparent antagonism between the herbicides.

Antagonism may be true biological antagonism where, for example, the biochemical effect of one herbicide is partially or wholly destroyed by the second herbicide. Antagonism may also be physical antagonism where either one herbicide or its formulation ingredients wholly or partially prevents the biological uptake of the second herbicide. It is frequently difficult, if not impossible, for the agriculturist to identify which of these types of antagonism is operative. Thus the term "apparent antagonism" is an appropriate one to describe the net, observable effect—a decrease in the efficacy of one herbicide when used in conjunction with another.

An example of apparent antagonism frequently occurs when grass herbicides and broadleaf herbicides are used simultaneously. Cyclohexenone herbicide A for example, is very effective in controlling a number of obnoxious grass species in various crops. Cyclohexenone A has little or no effect, however, on broadleaf weeds, where bentazon is very effective. When cyclohexenone A is used with the "standard" crop oil concentrate, control of POAAN and BROSE is greater than 90 percent control, a very acceptable value. There is no grass control at all in the presence of bentazon when the "standard" oil concentrate is used. When the crop oil concentrate of the subject invention is used, however, control is maintained at high levels. These results are summarized in Table I.

TABLE I

Effect of Oil Concentrates on Antagonism Between Cyclohexenone A and Bentazon

| Herbicide @ rate | Oil Concentrate @ rate | POAAN | FESAR | POAPR | BROSE | AVESA | OVERALL |
|---|---|---|---|---|---|---|---|
| Cyclohexenone A @ 75 g/ha | OC @ 2 l/ha | 91 | 95 | 97 | 91 | 99 | 92 |
|  | COC-1 @ 2 l/ha | 95 | 96 | 99 | 92 | 99 | 96 |
| Cyclohexenone A @ 75 g/ha + bentazon @ 70 g/ha | OC @ 2 l/ha | 0 | 94 | 96 | 0 | 94 | 40 |
|  | COC-1 @ 2 l/ha | 89 | 95 | 98 | 93 | 97 | 91 |

When normal rates of either sethoxydim or cycloxydim are used in conjunction with bentazon, control of several weed species, may be adversely effected. In Table II, sethoxydim is shown to be very effective on all weed species tested when used with the standard oil concentrate or with a commercially available nonionic surfactant, e.g. PLURAFAC ® LF700 nonionic surfactant. However when bentazon, (Basagran ® herbicide) is added, the control of all grass species decreases. TRZAX and HORVU control reaches totally unacceptable levels. Replacement of the oil concentrate or nonionic surfactant with the crop oil concentrate of the subject invention results in raising the level of control to substantially the same level as sethoxydim when used without bentazon.

TABLE II

Effect of Oil Concentrates on Herbicide Antagonism

| Herbicide @ rate | Concentrate (@ 2 l/ha) | Species: TRZAX | AVESA | LOLMU | HORVU | OVERALL |
|---|---|---|---|---|---|---|
| Sethoxydim @ 200 g/ha | OC | 90 | 98 | 97 | 83 | 88 |
|  | LF-700 | 93 | 99 | 98 | 84 | 90 |
|  | COC-1 | 94 | 99 | 99 | 85 | 90 |
| Sethoxydim @ 200 g/ha + | OC | 32 | 93 | 90 | 28 | 50 |
| bentazon @ 720 g/ha | LF-700 | 20 | 77 | 72 | 23 | 40 |
|  | COC-1 | 80 | 98 | 94 | 72 | 80 |

¹PLURAFAC LF-700 nonionic surfactant, a product of BASF Corporation, Parsippany, N.J.

As a further example, the addition of bentazon to tank mixes of cycloxydim and standard crop oil concentrate lowers overall weed control from 78 percent control, a quite acceptable level, to only 32 percent control, a level which is unacceptable. As Table IIa demonstrates, the use of COC-3 in place of the standard concentrate raises control to 73 percent. Thus the crop oil concentrate of the subject invention once again defeats the apparent antagonism displayed by the mix.

Not only are the crop oil concentrates efficient in defeating herbicide antagonism, they are valuable as highly effective crop oil concentrates in tank mixes containing but a single herbicide. The tables which follow illustrate the greater efficacy of the subject invention crop oil concentrates as compared to other concentrates.

TABLE IIa

Effect of Oil Concentrate on Cycloxydim/Bentazon Antagonism in Grass Control

| Herbicide | Oil Concentrate @ 1.5 l/ha | Species: DIGSA | ECHCG | ZEAMX | OVERALL |
|---|---|---|---|---|---|
| cycloxydim @ 50 g/ha | OC | 94 | 98 | 23 | 78 |
|  | COC-3 | 96 | 98 | 76 | 92 |
| cycloxydim @ 50 g/ha + | OC | 40 | 40 | 10 | 32 |
| bentazon @ 720 g/ha | COC-3 | 86 | 92 | 23 | 73 |

TABLE III

Grass Control by Cycloxydim at 100 g/ha

| Concentrate* | TRZAX | AVESA | LOLMU | HORVU | OVERALL |
|---|---|---|---|---|---|
| OC | 73 | 100 | 99 | 91 | 90 |
| COC-1 | 82 | 100 | 99 | 96 | 93 |
| COC-2 | 87 | 100 | 99 | 98 | 96 |

*at 1.5 l/ha

TABLE IV

Grass Control By Sethoxydim at 150 g/ha

| Concentrates | Species: TRZAX | AVESA | LOLMU | HORVU | OVERALL |
|---|---|---|---|---|---|
| OC | 30 | 92 | 86 | 30 | 62 |
| COC-1 | 73 | 99 | 98 | 68 | 85 |
| COC-2 | 75 | 99 | 98 | 77 | 87 |

*at 2.0 l/ha

TABLE V

Grass Control by Sethoxydim at 125 g/ha

| Concentrate* | TRZAX | AVESA | LOLMU | HORVU | OVERALL |
|---|---|---|---|---|---|
| OC | 77 | 99 | 99 | 65 | 79 |
| COC-1 | 90 | 99 | 99 | 86 | 92 |
| COC-2 | 89 | 95 | 99 | 84 | 92 |
| Sunflower oil methyl esters | 85 | 99 | 99 | 80 | 87 |

*at 2.0 l/ha

Tables III–V indicate that the crop oil concentrates of the subject invention are more effective than either the "standard" concentrate or sunflower oil methyl ester in achieving effective control of the grass species tested. This is particularly evident with regard to control of TRZAX (volunteer wheat). As certain grass species are more sensitive than others, the herbicide application rate would have to be adjusted for each species to permit demonstration of the greater efficacy of the subject invention crop oil concentrates for each individual weed species.

A major feature of the crop oil concentrates of the subject invention is that they allow retention of high levels of control while using less herbicide, thus decreasing costs and benefiting the environment. This is demonstrated in Table VI.

TABLE VI

Effect of Oil Concentrate on Efficacy of Sethoxydim Across Species[1]

| SPECIES | Oil Concentrate[2] | Sethoxydim Rate (g/ha) | | | |
|---|---|---|---|---|---|
| | | 7.0 | 3.5 | 1.7 | 0.8 |
| SETFA | OC | 100 | 30 | 0 | 0 |
| | COC-1 | 100 | 100 | 95 | 40 |
| DIGSA | OC | 50 | 20 | 0 | 0 |
| | COC-1 | 98 | 50 | 30 | 0 |
| BRAPP | OC | 100 | 100 | 30 | 0 |
| | COC-1 | 100 | 100 | 100 | 80 |
| AVEFA | OC | 98 | 0 | 0 | 0 |
| | COC-1 | 100 | 95 | 30 | 0 |
| PANTE | OC | 98 | 90 | 20 | 0 |
| | COC-1 | 100 | 98 | 90 | 20 |
| SETVI | OC | 100 | 90 | 40 | 0 |
| | COC-1 | 100 | 100 | 90 | 50 |
| SETLU | OC | 98 | 95 | 50 | 10 |
| | COC-1 | 100 | 95 | 85 | 30 |
| SORHA | OC | 90 | 70 | 20 | 10 |
| | COC-1 | 100 | 100 | 98 | 60 |
| ECHCG | OC | 100 | 100 | 90 | 10 |
| | COC-1 | 100 | 100 | 100 | 60 |
| ZEAMX | OC | 50 | 20 | 0 | 0 |
| | COC-1 | 100 | 100 | 50 | 20 |

[1]Greenhouse trials with exposure to direct sunlight
[2]OC applied at 2.3 l/ha, COC-1 applied at 4.6 l/ha.

In Table VII, the greater efficacy of the crop oil concentrate of the subject invention in controlling ECHCG (*echinochloa crus-galli*) is demonstrated. The data indicates that cycloxydim at 50 g/ha has greater efficacy when used with the subject invention crop oil concentrate at 0.5 l/ha than cycloxydim at 75 g/ha with the "standard" concentrate at 1.5 l/ha. It even outperforms cycloxydim at 50 g/ha when used in conjunction with 5.0 kg/ha of ammonium sulfate and the "standard" concentrate at 1.5 l/ha, which is often the treatment of choice to enhance efficacy of certain herbicides systems.

TABLE VII

Echinochloa Crus-galli Control Using Cycloxydim

| Cyclcxydim Rate, g/ha | OC[1] | COC-1[2] |
|---|---|---|
| 50 | 93 | 98 |
| 75 | 96 | 99 |
| 50 + ammonium sulfate @ 5.0 Kg/ha | 97 | |

[1]@1.5 l/ha
[2]@0.5 l/há

Table VIII below shows the effect of using the crop oil concentrate of the subject invention to aid in control of AVEFA and LOLMU in barley with three different cyclohexenone herbicides. In all cases, the degree of control is much higher with the crop oil concentrate of the subject invention than with the "standard" concentrate.

TABLE VIII

| | | Weed Control in Barley | | |
|---|---|---|---|---|
| Herbicide @ rate | Concen-trate* | Species: | | |
| | | LOLMU | AVEFA | OVERALL |
| Cyclohexenone B | OC | 68 | 65 | 67 |
| @ 200 g/ha | COC-2 | 87 | 95 | 94 |
| Cyclohexenone C | OC | 58 | 58 | 58 |
| @ 100 g/ha | COC-2 | 78 | 88 | 83 |
| Cyclohexenone D | OC | 47 | 50 | 48 |
| @ 50 g/ha | COC-2 | 79 | 94 | 86 |

*2 l/ha

Table IX demonstrates the improvement made possible by the crop oil concentrates of the subject invention when used for weed control in peas.

TABLE IX

Sethoxydim* Weed Control in Peas

| Concen-trate** | Species: | | | | OVER-ALL |
|---|---|---|---|---|---|
| | TRZAX | AVESA | LOLMU | HORVU | |
| OC | 30 | 92 | 86 | 30 | 62 |
| COC-1 | 73 | 99 | 98 | 68 | 85 |
| COC-2 | 75 | 99 | 98 | 77 | 87 |

*at 150 g/ha
**at 2 l/ha

In Table X below is demonstrated the effect of the crop oil concentrates of the subject invention when compared to the common, locally used concentrate, LOC, in the control of SORHA (*sorghum halepense*) with two cyclohexenone herbicides.

TABLE X

Cyclohexenone Control of *Sorghum halepense*

| Herbicide @ Rate | Concentrate @ Rate | % Control |
|---|---|---|
| Sethoxydim @ 370 g/ha | LOC @ 2 l/ha | 60 |
| | COC-1 @ 2 l/ha | 89 |
| | COC-1 @ 1.5 l/ha | 82 |
| Cycloxydim @ 200 g/ha | LOC @ 2 l/ha | 60 |
| | COC-1 @ 2 l/ha | 89 |
| | COC-1 @ 1.5 l/ha | 89 |

Tables XI–XIV demonstrate that the subject invention crop oil concentrates are effective with a wide variety of herbicides. The herbicidal efficacy was evaluated in Greenhouse trials with a predetermined optimum amount of oil concentrate. The weed species tested reflect real conditions as would be found in relevant crops.

TABLE XI

EFFICACY OF CROP OIL CONCENTRATES IN VARIOUS HERBICIDES

| Herbicide | Oil Concentrate | Species: | | | | | | | | |
|---|---|---|---|---|---|---|---|---|---|---|
| | | AVEFA | BRAPP | CHEAL | DAOTE | DATST | DIGSA | ECHCG | IPOLA | SETVI |
| haloxyfop-methyl @ 31 g/ha | OC @ 2.3 l/ha | 0 | — | — | — | — | 40 | 50 | — | — |
| | COC-1 @ 4.6 l/ha | 30 | — | — | — | — | 90 | 100 | — | — |
| fluazifop-P-butyl @ 25 g/ha | OC @ 2.3 l/ha | — | 90 | — | — | — | 40 | 40 | — | — |
| | COC-1 @ 4.6 l/ha | — | 98 | — | — | — | 80 | 85 | — | — |
| paraquat @ 140 g/ha | X-77[1] @ 0.5 l/ha | 85 | — | — | — | — | — | — | — | — |
| | COC-1 @ 2.3 l/ha | 100 | — | — | — | — | — | — | — | — |
| @ 9 g/ha | X-77 @ 0.5 l/ha | — | — | — | — | — | — | — | — | 45 |
| | COC-1 @ 2.3 l/ha | — | — | — | — | — | — | — | — | 65 |
| acifluorfen @ 18 g/ha | OC @ 2.3 l/ha | — | — | 15 | 25 | 90 | — | — | 40 | — |
| | COC-1 @ 2.3 l/ha | — | — | 85 | 78 | 100 | — | — | 93 | — |

TABLE XI-continued
EFFICACY OF CROP OIL CONCENTRATES IN VARIOUS HERBICIDES

| | | | | | | | | | | |
|---|---|---|---|---|---|---|---|---|---|---|
| @ 9 g/ha | OC @ 2.3 l/ha | — | — | 10 | 15 | 37 | — | — | 18 | — |
| | COC-1 @ 2.3 l/ha | | | 90 | 75 | 98 | | | 23 | |
| @ 4.5 g/ha | OC @ 2.3 l/ha | — | — | 5 | 5 | 12 | — | — | 10 | — |
| | COC-1 @ 2.3 l/ha | | | 80 | 38 | 20 | | | 10 | |

| | | Species: | |
|---|---|---|---|
| Herbicide | Oil Concentrate | SORHA | ZEAMX |
| haloxyfop-methyl @ 31 g/ha | OC @ 2.3 l/ha | — | 50 |
| | COC-1 @ 4.6 l/ha | — | 100 |
| fluazifop-P-butyl @ 25 g/ha | OC @ 2.3 l/ha | 50 | 96 |
| | COC-1 @ 4.6 l/ha | 98 | 99 |
| paraquat @ 140 g/ha | X-77[1] @ 0.5 l/ha | — | — |
| | COC-1 @ 2.3 l/ha | — | — |
| @ 9 g/ha | X-77 @ 0.5 l/ha | — | — |
| | COC-1 @ 2.3 l/ha | — | — |
| acifluorfen @ 18 g/ha | OC @ 2.3 l/ha | — | — |
| | COC-1 @ 2.3 l/ha | — | — |
| @ 9 g/ha | OC @ 2.3 l/ha | — | — |
| | COC-1 @ 2.3 l/ha | — | — |
| @ 4.5 g/ha | OC @ 2.3 l/ha | — | — |
| | COC-1 @ 2.3 l/ha | — | — |

[1]X-77 is a product of the Chevron Chemical Co., San Francisco, CA.

TABLE XII
Efficacy of Postemergence Broadleaf Herbicides in Presence of Oil Concentrates

| | | Species: | |
|---|---|---|---|
| Herbicide @ rate | Concentrate* | DAOTE | XANPE |
| bentazon @ 1.12 kg/ha | OC | 62 | |
| | COC-1 | 78 | |
| acifluorfen @ 36 g/ha | OC | | 77 |
| | COC-1 | | 98 |
| acifluorfen @ 40 g/ha + bentazon @ 1.12 kg/ha | OC | 73 | |
| | COC-1 | 98 | |

*at 2.3 l/ha

Table XIII and XIV show data from field trials indicating the superiority of oil concentrate of subject invention compared to "standard" concentrate.

TABLE XIII
Effect of Crop Oil Concentrates on Clumpcorn Control with Various Herbicides

| | | ZEAMX[1]: | |
|---|---|---|---|
| Herbicide @ rate | Concentrate @ 2.3 l/ha | 8–12" | 12+" |
| sethoxydim @ 168 g/ha | OC | 23 | 25 |
| | COC-2 | 60 | 70 |
| fluazifop-P-butyl @ 210 g/ha | OC | 78 | 80 |
| | COC-2 | 88 | 85 |
| Fluazifop-P-butyl @ 100 g/ha | OC | 60 | 65 |
| | COC-2 | 68 | 68 |
| Fenoxaprop-ethyl @ 112 g/ha | OC | 25 | 27 |
| | COC-2 | 60 | 70 |

[1]Zea mays clumpcorn of 8–12 and 12+ inches height

TABLE XIV
Effect of Crop Oil Concentrates on Clethodim[1] Control of Various Weed Species

| | Species: | | | | |
|---|---|---|---|---|---|
| Concentrate | FESAR | BROSE | POAPR | AVESA | OVERALL |
| OC @ 2 l/ha | 90 | 58 | 92 | 93 | 81 |
| COC-2 @ 2 l/ha | 94 | 84 | 92 | 95 | 90 |

[1]Clethodim @ 75 g/ha

The embodiments of the invention in which an exclusive privilege or property is claimed are defined as follows:

1. A process for decreasing the apparent antagonism exhibited by mixtures of two or more herbicides selected from the group consisting of cyclohexenone herbicides and benzothiadiazinonedioxide herbicides with respect to each other when applied to certain weed gases upon which antagonism of the herbicidal mixture is demonstrated comprising: adding thereto an effective amount of a crop oil concentrate comprising (a) from about 20 to about 90 weight percent of a lower alkanol ester of a long chain carboxylic acid having from 10 to 20 carbon atoms;

(b) from about 4 to about 40 weight percent of an anionic surfactant selected from the group consisting of the partial sulfate and phosphate esters and carboxylates of monohydroxyl-functional polyoxyalkylene ethers; and (c) from 2 to about 20 weight percent of a long chain carboxylic acid containing from about 10 to about 20 carbon atoms.

2. A process for decreasing apparent antagonism according to claim 1 wherein said crop oil concentrate further comprises up to about 140 weight percent based on the total weight of components a), b), and c), of (d) a hydrocarbon.

3. The process of claim 1 wherein the week grass is one or more of the following:
   poa annua;
   avena sativa;
   bromus secalinus;
   triticum aestivum;
   lolium multiflorum
   hordeum vulgare;
   digitoria sanguinalis;
   echinochloa crus-galli; or
   zea mays.

4. The process of claim 2 wherein the weed grass is
   poa annua;
   avena sativa;
   bromus secalinus;
   triticum aestivum;
   lolium multiflorum
   hordeum vulgare;
   digitoria sanguinalis;
   echinochloa crus-galli; or
   zea mays.

* * * * *